US010781293B2

(12) United States Patent
Girod Fullana et al.

(10) Patent No.: US 10,781,293 B2
(45) Date of Patent: Sep. 22, 2020

(54) PROCESS FOR PREPARING BIOCOMPATIBLE AND BIODEGRADABLE POROUS THREE-DIMENSIONAL POLYMER MATRICES AND USES THEREOF

(71) Applicants: CENTRE HOSPITALIER UNIVERSITAIRE DE TOULOUSE, Toulouse (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR); UNIVERSITE TOULOUSE III—Paul Sabatier, Toulouse (FR)

(72) Inventors: Sophie Girod Fullana, Auzeville Tolosane (FR); Brigitte Sallerin, Toulouse (FR); Raya Bushkalova, Toulouse (FR); Caroline Ceccaldi, Saint Antonin Noble Val (FR)

(73) Assignees: CENTRE HOSPITALIER UNIVERSITAIRE DE Toulouse, Toulouse (FR); CENTRE NATIONAL DE LA RECHERCHE Scientifique, Paris (FR)

(*) Notice: Subject to any disclaimer, the term of this patent is extended or adjusted under 35 U.S.C. 154(b) by 176 days.

(21) Appl. No.: 15/747,281

(22) PCT Filed: Jul. 27, 2016

(86) PCT No.: PCT/FR2016/051954
§ 371 (c)(1),
(2) Date: Jan. 24, 2018

(87) PCT Pub. No.: WO2017/017379
PCT Pub. Date: Feb. 2, 2017

(65) Prior Publication Data
US 2018/0215892 A1  Aug. 2, 2018

(30) Foreign Application Priority Data

Jul. 30, 2015  (FR) .................................. 15 57339

(51) Int. Cl.
*C08J 9/28*  (2006.01)
*A61L 27/56*  (2006.01)
(Continued)

(52) U.S. Cl.
CPC ................. *C08J 9/28* (2013.01); *A61L 27/20* (2013.01); *A61L 27/26* (2013.01);
(Continued)

(58) Field of Classification Search
CPC ... C12N 2533/72; C12N 2533/74; C08L 5/08; C08L 5/04
See application file for complete search history.

(56) References Cited

U.S. PATENT DOCUMENTS

2005/0042263 A1  2/2005  Damien

FOREIGN PATENT DOCUMENTS

WO    2008092228    8/2008

OTHER PUBLICATIONS

International search report dated Jun. 16, 2016, for FR 1557339.
(Continued)

*Primary Examiner* — Kortney L. Klinkel
(74) *Attorney, Agent, or Firm* — IPSILON USA, LLP

(57) ABSTRACT

The present invention relates to a process for preparing a biocompatible and biodegradable, porous three-dimensional polymer matrix, to the porous polymer matrix obtained by means of such a process, and also to the uses thereof, in particular as a support and for cell culture or in regenerative medicine, and in particular for cell therapy, in particular cardiac cell therapy.

13 Claims, 4 Drawing Sheets

(51) Int. Cl.
- *C08J 9/00* (2006.01)
- *C08J 9/08* (2006.01)
- *A61L 27/26* (2006.01)
- *A61L 27/58* (2006.01)
- *A61L 27/20* (2006.01)
- *A61L 27/38* (2006.01)
- *A61L 27/54* (2006.01)

(52) U.S. Cl.
CPC ........... *A61L 27/3834* (2013.01); *A61L 27/54* (2013.01); *A61L 27/56* (2013.01); *A61L 27/58* (2013.01); *C08J 9/0061* (2013.01); *C08J 9/08* (2013.01); *A61L 2300/412* (2013.01); *A61L 2300/64* (2013.01); *A61L 2400/08* (2013.01); *A61L 2430/20* (2013.01); *C08J 2201/026* (2013.01); *C08J 2201/0484* (2013.01); *C08J 2201/0546* (2013.01); *C08J 2203/02* (2013.01); *C08J 2205/044* (2013.01); *C08J 2205/05* (2013.01); *C08J 2207/10* (2013.01); *C08J 2305/00* (2013.01); *C08J 2305/04* (2013.01); *C08J 2405/00* (2013.01); *C08J 2405/04* (2013.01); *C08J 2405/08* (2013.01)

(56) References Cited

OTHER PUBLICATIONS

Fabrication and characterization of natural origin chitosan-gelatin-alginate composite scaffold, Sharma et al. Journal of Applied Polymer Science 127(4) 2012, 3228-3241.

Hepatocyte-specific porous polymer-scaffolds of alginate/galactosylated chitosan sponge, Jun Yang et al., Biotechnology Letters, 2001, 1385-1389.

PROCESS FOR PREPARING BIOCOMPATIBLE AND BIODEGRADABLE POROUS THREE-DIMENSIONAL POLYMER MATRICES AND USES THEREOF

RELATED APPLICATION

This application is a National Phase of PCT/FR2016/051954, filed on Jul. 27, 2016, which in turn claims the benefit of priority from French Patent application No. 15 57339, filed on Jul. 30, 2015 the entirety of which are incorporated by reference.

FIELD OF THE INVENTION

The present invention relates to a process for preparing a biocompatible and biodegradable, porous three-dimensional polymer matrix, to the porous polymer matrix obtained by means of such a process, and also to the uses thereof, in particular as a support and for the cell culture or in regenerative medicine, in particular for cardiac cell therapy.

DESCRIPTION OF THE RELATED ART

Cell therapy is a promising therapeutic strategy for cardiac ischemic syndromes. Indeed, the latter are already treated in patients by autologous graft of mesenchymal stem cells (MSCs) directly injected into the damaged organ, but the low cell survival rate (<15%) in the three days following the injection limits the beneficial effects thereof. In point of fact, the functional recovery of the damaged organ correlates directly with the number of surviving MSCs; recent studies have shown that the regeneration of the infarcted organ is thought to be mainly due to their paracrine effects. In this context, maintaining MSC viability and functionality appears to be a major challenge for improving the benefit/risk ratio of the treatment of ischemias by cell therapy.

The development of porous biomaterials capable of generating a biomimetic environment favourable to maintaining MSCs, while at the same time allowing administration in "patch" form at the surface of the damaged organ, constitutes an advance in this field, and is the subject of intensive research.

Such an approach, which no longer requires the injection of cells directly to the heart, would make it possible to avoid: 1) the mortality of the injected cells, 2) the side effects associated with intra-parenchymal injection (in particular bleeding) and 3) the danger of the transformation of the mesenchymal stem cells into an unwanted phenotype (osteoblast, chondroblast, adipocyte or, worse, cancer cells). For this, it is necessary to develop 3-dimensional (3D) biomimetic porous materials which localize the cells on the damaged site, protect them during implantation and maintain them at an undifferentiated state in order to prolong their paracrine effects. To do this, the three-dimensional porous materials must meet precise specifications regarding their porosity, their mechanical strength and their elasticity.

Polymer matrices are widely used in the tissue engineering sector. Generally, two major types of matrices are distinguished: those which make use of polymers of synthetic origin and those based on polymers of natural origin, the latter being preferred because of their better biocompatibility and the possibility of synthesizing matrices without organic solvents or toxic reaction intermediates, at temperatures and pHs that are compatible with cell survival.

Over the past 20 years, alginate has proved to be the polymer of choice in tissue engineering because of its excellent biocompatibility in vivo, attributed to its polysaccharide nature, and to the fact that the structure of its network is similar to that of the extracellular matrix (ECM) of living tissues. For example, Andersen T. et al. (BioMacromolecules, 2012, 13, 3703-3710) describe alginate-based macroporous sponges with open and interconnected pores and also the potential uses thereof for cell encapsulation, drug delivery and healing. These macroporous sponges are prepared by gelling a solution of alginate, of calcium carbonate and of a plasticizer in the presence of a divalent cation, said solution being stirred beforehand at high speed so as to incorporate air bubbles therein. The gel obtained is then dehydrated by drying in air at 80° C. to give a highly porous structure called xerogel. These alginate xerogels are of limited commercial interest for all the applications requiring an implantation. This is because they have a porosity that is favourable to cell culture but that, on the other hand, gives them, in return, a low mechanical strength. Furthermore, it is difficult to maintain their initial 3D structuring (responsible for their biocompatibility, for their biomimetics and for their seeding capacity) after this type of drying.

International application WO 2007/103208 describes a process for preparing open-porosity biodegradable sponges based on a polysaccharide such as chitosan or hyaluronic acid, consisting in forming a wet foam from an aqueous dispersion comprising such a polysaccharide, a foaming agent and optionally one or more gel-forming ions, a plasticizer, a crosslinking agent and a pH modifier, then in moulding and air-drying the foam thus obtained. Just like the previous alginate sponges, the polysaccharides sponges thus obtained (xerogels) have an open porous network but insufficient mechanical properties for easy implantation.

U.S. Pat. No. 6,425,918 describes, moreover, a process for preparing matrices based on polysaccharides such as alginates, carrageenans, gellan gum, xanthan gum, chitosan, etc., consisting, in a first step, in gelling a solution of a polysaccharide in the presence of a crosslinking agent, then, in a second step, in freezing the gel thus obtained, before drying it by lyophilization in a third step. The matrices obtained according to this process (cryogels) exhibit improved mechanical strength compared with the alginate xerogels described in Andersen T. et al. (mentioned above). However, it is difficult, by means of this process, to modulate the porosity generated by the method of freezing and drying, and to adapt it to the envisaged uses; the possibilities for controlling the sizes of the pores obtained are limited.

A matrix composed of a combination of three alginate/chitosan/gelatin polymers has also already been proposed, in particular in the article by Chhavi Sharma et al., Journal of Applied Polymer Science, 2012, Vol. 127(4), pages 3228-3241. This matrix is prepared from a foam obtained by stirring an aqueous solution of alginate (2%) and of gelatin (5%) without using any surfactant but in the presence of $NaHCO_3$ to generate gas, a solution of glutaraldehyde then being added to said foam. The crosslinked alginate/gelatin foam is then added, in extruded ball form, to an acid solution of chitosan containing $CaCl_2$ (crosslinking agent for the alginate). The balls are then exposed to a vacuum in order to modify the porosity thereof. The use of glutaraldehyde makes it possible to crosslink the gelatin or the chitosan by means of covalent bonds. However, glutaraldehyde is toxic to cells. The addition of chitosan in a second step results in the formation of a shell around the microspheres and in a non-homogeneous distribution thereof within the structure of the final material. Finally, the simple use of sodium bicarbonate results in the formation of bubbles and therefore in a non-interconnected porosity in the balls. The vacuum-drying step used at the end of the process causes interconnection of the pores via the breaking of the thinnest walls of the porous structure, but results in a population of pores with random sizes, which are not necessarily suitable for cell culture applications.

OBJECTS AND SUMMARY

There is therefore a need for biocompatible and biodegradable polymer matrices which are highly porous while at the same time having good mechanical properties.

The inventors therefore gave themselves the aim of developing a preparation process which makes it possible to obtain biocompatible and biodegradable, three-dimensional polymer matrices which allow both good mechanical strength properties while at the same time comprising a network of open and interconnected pores corresponding to the seeding-capacity, biocompatibility and biomimetic criteria in order to enable their use as a cell support and/or for cell culture, and also in tissue therapy, in particular in cardiac tissue therapy.

The first subject of the present invention is therefore a process for preparing a biocompatible and biodegradable polymer matrix comprising a network of open and interconnected pores, said process comprising at least the following steps:

1) preparing an aqueous solution comprising at least one biocompatible anionic polysaccharide and at least one biocompatible cationic polymer, 2) mechanically stirring said solution obtained above in the preceding step, in the presence of a foaming agent or of a pressurized gas, so as to form a foam, 3) freezing the foam obtained above in the preceding step, so as to obtain a frozen foam, 4) gelling the frozen foam obtained above in the preceding step, by adding, to said foam, at least one gelling agent in solution in a solvent, so as to obtain a gelled foam, 5) dehydrating the gelled foam obtained above in the preceding step, so as to obtain a dehydrated gelled foam, then 6) drying the dehydrated gelled foam obtained above in the preceding step, by treatment with supercritical $CO_2$, so as to obtain said polymer matrix.

By virtue of the process in accordance with the invention, it is now possible to prepare biocompatible and biodegradable polymer matrices comprising a network of open and interconnected pores enabling their use for cell culture and also having a mechanical strength and an elasticity sufficient to enable their use in cell therapy, in particular in cardiac cell therapy.

According to the invention, the term "biocompatible" used in the present description to describe said polymer matrix or a substance, such as for example an anionic polysaccharide or a cationic polymer, means that said material or said substance does not interfere with and does not degrade the biological medium in which it is used.

For the purposes of the present invention, the expression "open and interconnected pores" means that the polymer matrix has an open porosity, that is to say a porosity that can be accessed from the outside of the matrix, and that said pores communicate with one another to form a three-dimensional network.

The biocompatible anionic polysaccharide(s) that can be used according to the invention preferably have an average molecular weight ($Mw_A$) of greater than or equal to 75 000 Daltons, preferably ranging from 75 000 to 250 000 Daltons approximately, and even more preferentially from 140 000 to 240 000 Daltons approximately.

The biocompatible anionic polysaccharide(s) that can be used according to the invention are preferably chosen from alginates and modified alginates, pectins, cellulose-based derivatives, polysaccharide gums such as agar-agar, xanthan gum and gellan gum, carrageenans, modified dextrans and hyaluronic acid.

According to one preferred embodiment of the invention, the biocompatible anionic polysaccharide(s) are chosen from alginates and modified alginates.

Among the alginates, preference is most particularly given to alginates comprising from 32% to 61% of mannuronic acid (M) units and from 39% to 68% of guluronic acid (G) units relative to the total number of units constituting said alginates, and in which the M/G ratio ranges from 0.47 to 1.56.

Among such alginates, mention may in particular be made of sodium alginates comprising at least 60% by number of G units, such as the products sold under the trade names Pronova UP MVG®, Pronova UP LVG®, Alginate SLG20® and Alginate SLG100® by the company Novamatrix, alginates comprising at least 50% by number of M units, such as the products sold under the trade names Pronova UP MVM®, Pronova UP LVM®, Alginate SLM20® and Alginate SLM100® by the company Novamatrix, or else the sodium alginates sold under the trade names Alginate Medium Viscosity and Alginate High Viscosity by the company Sigma-Aldrich.

According to one most particularly preferred embodiment of the invention, the biocompatible anionic polysaccharide is a sodium alginate having a viscosity of greater than or equal to 2000 mPa·s and an average molecular weight of between 80 000 and 120 000 Da inclusive.

For the purposes of the present invention, the term "modified alginate" is intended to mean an alginate of which the basic structure is functionalized with one or more groups, in particular with one or more peptides such as, for example, tripeptides composed of L-arginine, of glycine and of L-aspartic acid (RGD peptides), which are peptides involved in cell adhesion. By way of example, such modified alginates are for example sold under the trade names Novatach®G RGD, Novatach®M RGD, Novatach®G VAPG and Novatach®M REGV by the company NovaMatrix.

According to one preferred embodiment of the invention, the amount of anionic polysaccharides present in the aqueous solution of step 1) ranges from 0.5% to 8% by weight approximately, and even more preferentially from 1% to 3% by weight approximately, relative to the total weight of said aqueous solution.

The biocompatible cationic polymer(s) that can be used according to the invention preferably have an average molecular weight ($Mw_C$) of greater than or equal to 100 000 Daltons, more preferentially ranging from 150 000 to 600 000 Daltons approximately, and even more preferentially from 190 000 to 310 000 Daltons approximately.

The biocompatible cationic polymer(s) that can be used according to the present invention are preferably chosen from cationic polysaccharides, in particular from the group comprising chitosan, particular saline forms of chitosan and chitosan derivatives; and polymers having basic reactive groups such as amine or imine groups, among which mention may be made of polyethyleneimines, poly(L-lysines), poly(vinylamines), poly(amino acids) and poly(alkylamines).

The biocompatible cationic polymer(s) are preferably chosen from chitosan, particular saline forms of chitosan and chitosan derivatives. Mention may in particular be made of the chitosans sold under the trade names Chitosan Low Molecular Weight, Chitosan Medium Molecular Weight and Chitosan High Molecular Weight, Chitosan High Purity Mw 60 000-120 000, Chitosan High Purity Mw 110 000-150 000 and Chitosan High Purity Mw 140 000-220 000 by the company Sigma-Aldrich, or else Protasan UP CL 113, 114, 213 and 214 by the company NovaMatrix. Among these chitosans, preference is most particularly given to chitosans having a viscosity of from 200 to 800 mPa-s approximately, an average molecular weight of between 190 000 and 310 000 Da inclusive, and a degree of deacetylation of greater than 80%.

The particular saline forms of chitosan (that can also be called chitosan salts) can in particular be chosen from chitosan chloride, lactate, acetate and glutamate.

For the purposes of the present invention, the term "chitosan derivative" is intended to mean a chitosan of which the basic structure is functionalized with one or more functional groups, in particular with one or more groups chosen from carboxymethyl or hydroxybutyl groups or else a glyceryl phosphate-hydroxyethylcellulose group. By way of examples of such chitosan derivatives, mention may in particular be made of the products sold under the trade name Chitoscience® or Chitoceuticals Carboxymethylchitosan® by the company HMC+.

According to one preferred embodiment of the invention, the amount of cationic polymers present in the aqueous solution of step 1) ranges from 0.5% to 15% by weight approximately, and even more preferentially from 1% to 2.25% by weight approximately, relative to the total weight of said aqueous composition.

According to one preferred embodiment of the invention, the weight ratio of anionic polysaccharides ($W_{AP}$)/cationic polymers ($W_{CP}$) present in the aqueous solution of step 1) ranges from 20/80 to 80/20, and even more preferentially from 40/60 to 60/40 approximately.

The total concentration of polymers present in the aqueous solution of step 1), that is to say the sum of the amounts of anionic polysaccharides and of cationic polymers, preferably ranges from 1% to 10% by weight approximately, and even more preferentially from 1.5% to 3.75% by weight approximately, relative to the weight of the aqueous solution.

In addition to the anionic polysaccharide(s) and the cationic polymer(s), the aqueous solution prepared during step 1) preferably comprises at least one hydrophilic surfactant, the presence of which makes it possible to stabilize the foam formed in step 2).

For the purposes of the present invention, the term "hydrophilic surfactant" is intended to mean a surfactant which has an HLB ("Hydrophilic-Lipophilic Balance" of greater than or equal to 8, and preferably greater than or equal to 12. Their presence in the aqueous solution prepared in step 1) makes it possible to stabilize the foam formed during step 2).

The hydrophilic surfactant(s) are preferably chosen from non-ionic surfactants.

Among such non-ionic surfactants, mention may in particular be made of ethoxylated fatty acid esters of sorbitan (polysorbates) such as the products sold under the trade names Eumulgin® SML20 and, SMS20 by the company BASF, Montanox® 20 PPI, Montanox® 20 API and Montanox® 80 PPI by the company SEPPIC, Alkest® TW20, TW60, TW80, TW80 K and TW327 by the company Univar, Carnacel® TW20 and TW80 by the company Quimica Delta, and Tween® 20, 40, 60, 65, 80 and 85 by the company Sigma-Aldrich; polyoxyethylene-polyoxypropylene nonionic block copolymers (also called poloxamers) such as the products sold under the trade names Pluronic®, in particular Pluronic® F68, Pluronic® F108 and Pluronic® F127, by the company Sigma-Aldrich, or Synperonic® or Kolliphor® also by the company Sigma-Aldrich; cellulose derivatives such as hydroxypropylmethylcellulose; glucosides and alkanolamides.

The hydrophilic surfactant(s) can also be chosen from anionic surfactants, and in particular from sodium dodecyl sulfate, such as the products sold under the trade names Triton®, in particular Triton® X-405 by the company Sigma-Aldrich, and cetyltrimethylammonium bromide (known by the acronym CTAB).

More rarely, the hydrophilic surfactant(s) can be chosen from certain cationic polymers such as, for example, polyquaterniums, for instance in particular Polyquaternium-10.

Finally, proteins such as albumin and gelatin can also act as a hydrophilic surfactant.

According to one preferred embodiment of the invention, the hydrophilic surfactant is a non-ionic surfactant, and even more preferentially a polysorbate or a poloxamer The hydrophilic surfactant(s) preferably represent from 0.01% to 5% by weight, and even more preferentially 1% by weight approximately, relative to the total weight of the aqueous solution of step 1).

Although it is not obligatory, the aqueous solution prepared in step 1) can also contain one or more plasticizers.

In this case, the plasticizer(s) are preferably chosen from glycerol, sorbitol and a mixture thereof.

When they are used, the ratio of the plasticizer(s) relative to the polymers in aqueous solution prepared in step 1) can range from 10:1 to 2:1, preferentially from 8:1 to 3:1, and even more specifically from 6:1 to 4:1.

The mechanical stirring carried out during step 2) is preferably carried out at a rotational speed of greater than or equal to 1500 revolutions per minute (rpm), and even more preferentially at a rotational speed ranging from 1500 to 2100 rpm approximately.

The mechanical stirring time generally ranges from 5 to 120 minutes approximately. It is typically approximately 30 minutes.

The mechanical stirring is preferably carried out using a conventional blade apparatus.

According to a first embodiment of step 2), the foam is formed in the presence of a foaming agent which is therefore added to the solution prepared in step 1) just before carrying out step 2).

In this case, the foaming agent (also called "pore-forming agent" or "gas-generating agent") is preferably chosen from sodium bicarbonate and sodium carbonate, and the aqueous solution of step 1) is then brought to an acid pH, preferably ranging from 4.0 to 6.5, by adding at least one acidifying agent.

According to this first embodiment of step 2), the foaming agent then preferably represents from 0.5% to 5% by weight approximately, and even more preferentially from 1% to 2% by weight approximately, relative to the total weight of the aqueous solution prepared in step 1).

The addition of an acidifying agent makes it possible to obtain a release of gas from the foaming agent present in the aqueous solution.

The acidifying agent can for example be chosen from acetic acid, adipic acid, tartaric acid, glucono-δ-lactone and hydrogen peroxide.

In this case, the acidifying agent (except hydrogen peroxide) preferably represents from 0.05% to 15% by weight approximately, relative to the total weight of the aqueous solution. If the acidifying agent is hydrogen peroxide, then its concentration can range up to 40% by weight approximately, relative to the total weight of the aqueous solution.

According to a second embodiment of step 2), the foam is formed by introducing a pressurized gas into the aqueous solution prepared in step 1).

In this case, the gas is for example chosen from air, argon and carbon dioxide.

According to this second embodiment, the pressure at which said gas is introduced can range from 1 to 100 bar approximately.

The time taken to introduce said pressurized gas into the aqueous solution can range from 20 min to 2 h approximately.

The freezing of step 3) is preferably carried out by bringing the foam obtained in step 2) to a temperature of less than or equal to −10° C. approximately, and even more preferentially to a temperature ranging from −18 to −20° C. approximately.

According to one particular and preferred embodiment, the freezing step 3) is carried out by maintaining the foam obtained in step 2) at a temperature of approximately −18° C. for 8 to 24 hours.

According to another particular embodiment, the freezing step 3) is carried out by dipping the foam obtained in step 2) in a liquid nitrogen bath at a temperature of −180° C. In this case, the freezing is rapid, of the order of a few seconds.

During the freezing step, the foam obtained in step 2) can be introduced into a mould so as to give said foam a particular shape, after freezing.

According to one particular embodiment of the process in accordance with the invention, the freezing step 3) can be followed by a step 3a) of lyophilizing the frozen foam obtained at the end of step 3).

In this case, the lyophilization step 3a) can be carried out under vacuum at a temperature ranging from −40 to −50° C. approximately and at a pressure ranging from 10 to 100 μm of mercury approximately.

The gelling agent used during step 4) of gelling the frozen foam is preferably a solution of at least one salt of a divalent or trivalent cation in a solvent. Such cations are preferably chosen from inorganic cations such as copper, calcium, aluminium, magnesium, strontium, barium, zinc or chromium, and also from organic cations such as alkylammonium salts, polyethyleneimine, poly(vinylamine), poly(amino acids) and poly(alkylamines).

The solvent of the gelling agent solution is preferably water, which may or may not be buffered.

According to one preferred embodiment of the invention, the gelling agent is an aqueous solution of calcium chloride, of strontium chloride, of calcium gluconate, of calcium carbonate or of strontium carbonate.

The concentration of the gelling agent solution can range from 0.005 M to 1 M approximately, and preferably from 0.05 to 1 M approximately.

At the end of step 4), the foam is preferably washed several times so as to remove the surfactant, for example using a solution of neutral pH, such as a buffer solution, for example a buffer based on 4-(2-hydroxyethyl)-1-piperazine ethanesulfonic acid (HEPES buffer).

Step 5) of dehydrating the gelled foam obtained in step 4) is preferably carried out gradually, by immersing said gelled foam in successive baths of absolute ethanol of increasing concentrations. By way of example, the dehydration of the gelled foam can be carried out by immersions in 3 baths of absolute ethanol at 20%, then 3 baths of absolute ethanol at 40%, then 3 baths of absolute ethanol at 80%, then, to finish, 3 baths of absolute ethanol at 100%, each of the immersions lasting from 10 to 15 minutes approximately.

Step 6) of drying, with supercritical $CO_2$, the dehydrated foam obtained at the end of step 5) is preferably carried out at a temperature ranging from 35 to 50° C. approximately, and at a pressure ranging from 45 to 95 bar approximately.

According to one particular and preferred embodiment, the step of drying the dehydrated foam with supercritical $CO_2$ is carried out at a temperature of approximately 44° C., at approximately 85 bar of pressure, for approximately 25 minutes.

When the dehydration step 6) is finished, the polymer matrix is ready to be used or stored for subsequent use. Before use, said matrix is preferably sterilized according to the methods well known to those skilled in the art and such as, for example, exposure to UV-rays, γ-irradiation, the use of pulsed or non-pulsed electron beams, or of ethylene oxide, autoclaving or contact with an alcohol or with a gas of formula NOx, or sterilization with plasma gas (Sterrad®) as long as none of these methods affects the properties of the final matrix or the characteristics of is these components.

The biocompatible and biodegradable polymer matrix obtained by carrying out the process as defined according to the first subject of the invention is novel in itself and, in this respect, constitutes the second subject of the invention.

A subject of the invention is therefore also a biocompatible and biodegradable polymer matrix obtained by carrying out the process in accordance with the present invention, said matrix being characterized in that it is in the form of a honeycombed material consisting of a porous polymer matrix resulting from the gelling of a foam of at least one biocompatible anionic polysaccharide and of at least one biocompatible cationic polymer, and in that said matrix:

comprises open and interconnected pores having an average dimension dA ranging from 0.2 μm to 400 μm;

has a pore volume ranging from 60% to 98% of the total volume of the matrix;

has an elastic modulus at 50% deformation ($E_{50\%}$) ranging from 1 to 100 kPa.

The elastic modulus at 50% deformation $E_{50\%}$ is determined using a texturometer sold under the trade name TA-XT2 Texture Analyser by the company Stable Micro Systems, with a cylindrical Plexiglas® (poly(methyl methacrylate)) piston which has a diameter of 20 mm and a compression speed of 2 mm/s for measuring the force required to compress a sample of polymer matrix to 50% of its initial height. The elastic modulus at 50% deformation is then calculated by applying the following formula:

$$E_{50\%} = \frac{(F_{50\%}/S)}{0.5} \times 1000$$

in which $E_{50\%}$ and $F_{50\%}$ are respectively the elastic modulus (in kPa) and the force (in N) required to obtain 50% deformation, and S is the surface area of the sample of polymer matrix (in mm²) in contact with the piston. Such a method has for example been described by Shapiro L. et al. (Biomaterials 1997, 18, 583-590).

According to one preferred embodiment of this material, the compressive elastic modulus ranges from 30 to 45 kPa.

Moreover, said polymer matrix in the rehydrated state preferably has a tensile Young's modulus ranging from 0.3 to 20 kPa, preferentially from 0.5 to 15 kPa and even more preferentially from 1 to 10 kPa. The measurements of tensile strength of the polymer matrices in accordance with the invention were carried out after rehydration of dumbbell-shaped samples in a complete alpha "Minimum Essential Medium" (MEM) (complete α MEM) until complete swelling was obtained. The measurements were carried out using a TAXT2 texturometer equipped with jaws, according to the protocol described in the article by Andersen et al., Biomacromolecules, 2012 (standard ASTM D638-10 (Type I)).

Finally, said polymer matrix preferably has storage (G') and loss (G") moduli ranging from 100 to 25 000 Pa.

G* is a rheological parameter called complex modulus. When a material is subjected to a dynamic shear test, it is noted that there is a phase shift between the stress applied and the deformation of the material. This reflects viscoelastic phenomena of energy storage (expressed via the modulus G', called storage modulus) and of energy dissipation (expressed via the modulus G" called loss modulus). The moduli G' and G" are measured in an (oscillatory) dynamic-mode rheological test according to the method described by Kong H. J. et al. (Polymer, 2002, 43, 6239-6246).

Likewise according to one preferred embodiment of this material, the moduli (G') and (G") range from 12 000 to 25 000 Pa for G' and from 1000 to 3000 kPa for G".

As previously indicated, the very nature of the material in accordance with the invention (high-porosity biocompatible polymer matrix) makes its use for cell culture particularly advantageous.

Consequently, a third subject of the invention is the use of the biocompatible and biodegradable polymer matrix as obtained by means of the process as defined according to the first subject of the invention or as defined in the second subject of the invention, as a support for animal or human cells and/or for the culture of animal or human cells in vitro, in particular of undifferentiated mammalian cells such as, for example, mesenchymal stem cells.

Indeed, the studies carried out by the inventors have shown that such a matrix constitutes a porous environment favourable to the viability and the maintaining of the functionalities of stem cells. Furthermore, it is possible to vary the porosity and the mechanical properties of the matrices of the invention within the ranges indicated above according to the choice of the nature of the polymers used for preparing it and to the type of cells that it is desired to support or culture.

DETAILED DESCRIPTION

Figure 1:
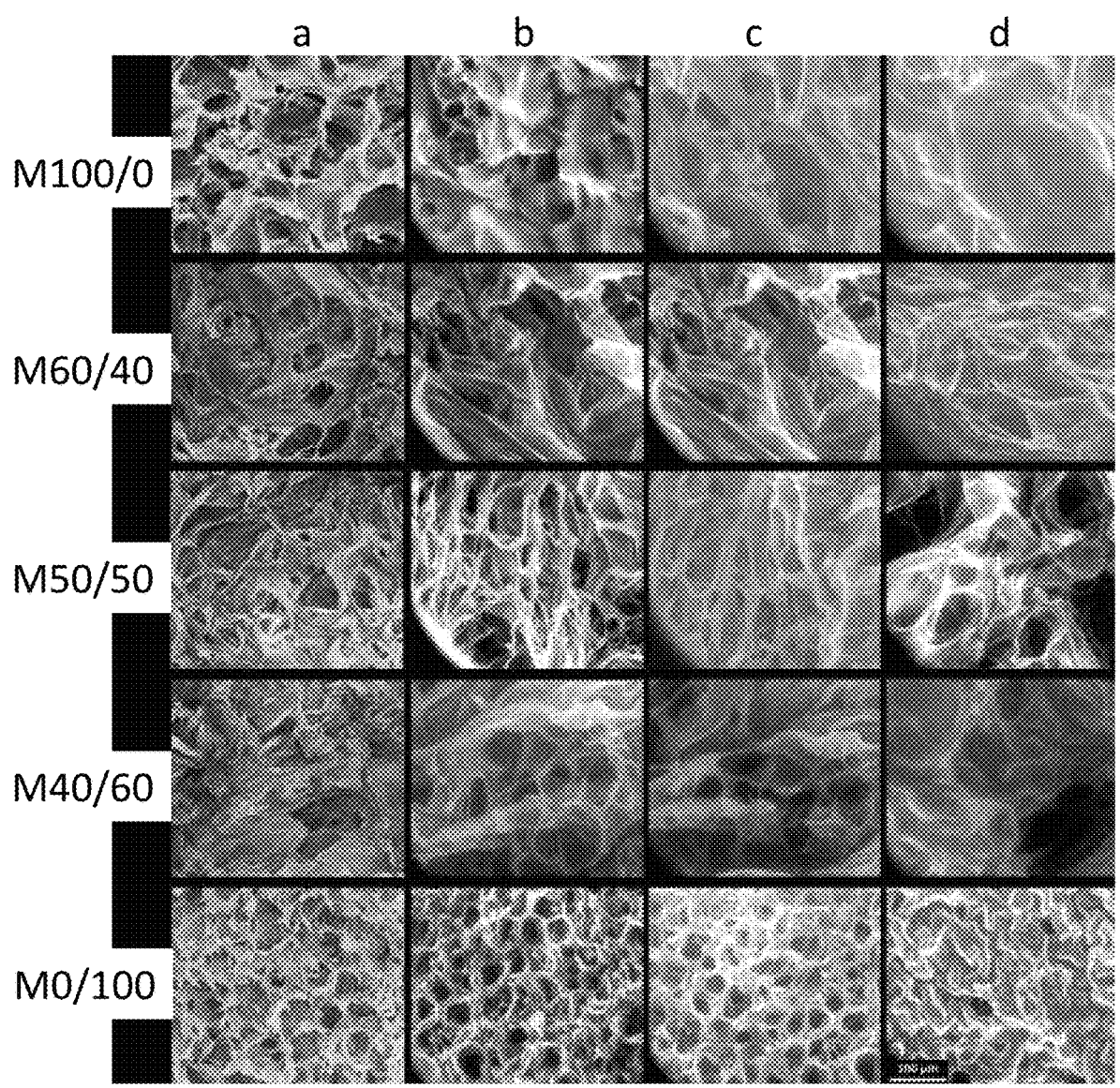
FIGS. 1a-1d are images of microscopic appearance of the matrices obtained in example 1 in accordance with one embodiment

Thus, a fourth subject of the invention is also a cell support comprising a porous polymer matrix containing animal or human cells, in particular undifferentiated mammalian cells, said support being characterized in that the porous polymer matrix is a matrix as obtained according to the process as defined according to the first subject of the invention or as defined in the second subject of the invention, and in that said cells are predominantly present in the pores of said matrix.

The excellent biocompatibility and the mechanical properties of such a cell support make its use in tissue therapy, and in particular in cardiac tissue therapy, particularly advantageous.

Thus, a fifth subject of the invention is also the cell support as defined according to the fourth subject of the invention, for use in regenerative medicine, in particular in cell therapy, in particular in cardiac cell therapy.

Such a support makes it possible, after implantation, in particular at the level of a cardiac muscle lesion, to localize the cells on the implantation site, while at the same time protecting them during implantation and while maintaining them in an undifferentiated state so as to prolong their paracrine effects.

The present invention is illustrated by the following implementation examples, to which it is not however limited.

EXAMPLES

The starting materials used in the examples which follow are listed below:

Sodium alginate from brown algae, of average molecular weight between 80 000 and 120 000 Da, and of viscosity≥2000 mPa-s (at 2% by weight in water, and at 25° C.), sold under the trade name Alginic acid sodium salt from brown algae—Medium viscosity by the company Sigma-Aldrich;

Deacetylated chitosan at 80%, of average molecular weight between 190 000 and 300 000 Da, of viscosity between 200 and 800 mPa-s (at 1% by weight in 1% acetic acid and at 25° C.), sold under the trade name Chitosan medium molecular weight by the company Aldrich;

NaCl and calcium carbonate (the company BDH Prolabo);

pure acetic acid (the company Fisher Chemical);

absolute ethanol, HEPES buffer (the company Sigma-Aldrich).

Physicochemical Characterizations

Scanning Electron Microscopy (SEM):

The polymer matrices prepared in the examples which follow were metallized with silver by argon sputtering using a machine sold under the trade name Sputter Coater S 150B® by the company Edwards, then observed using a JSM-6400 scanning electron microscope from the company Jeol under a voltage of 10 kV. For each sample, 10 measurements of the pore diameter were carried out at the surface and in cross section and then the mean was calculated.

Environmental Scanning Electron Microscopy:

Cubic samples of approximate dimensions 5×5×2.5 mm were cut out from the polymer matrices prepared in the examples which follow and were introduced in the dry state into the chamber of a Quanta® 250 FEG ESEM microscope from the company FEI. The samples were gradually hydrated therein by controlling the level of humidity in the chamber, which gradually increases from 85% to 99%, by adjusting the water vapour pressure. The acceleration voltage was adjusted to 15 kV and the temperature to 2° C.

Mechanical Strength (Uniaxial Compression Test):

Uniaxial compression tests were carried out on samples of the polymer matrices prepared in the examples which follow, after hydration for 24 hours in a cell culture medium. Each sample was subjected to 3 uniaxial compression tests and the measurements were carried out in triplicate. The measurements were carried out using a texturometer sold under the trade name TA-XT2 Texture Analyser by the company Stable Micro Systems, with a cylindrical aluminium piston which has a diameter of 20 mm and a compression speed of 2 mm/s for measuring the force required to compress the samples to 50% of their initial height. The elastic modulus at 50% deformation was then calculated by applying the following formula:

$$E_{50\%} = \frac{(F_{50\%}/S)}{0.5} \times 1000$$

in which $E_{50\%}$ and $F_{50\%}$ are respectively the elastic modulus (in kPa) and the force (in N) required to obtain 50% deformation, and S is the surface area of the sample (in $mm^2$) in contact with the piston.

Mechanical Strength (Uniaxial Tensile Test):

In the examples which follow, tensile tests were carried out on the dumbbell-shaped samples of the polymer matrices (according to standard ASTM D638-10 (Type I)), after rehydration for 24 hours in the cell culture medium. The Young's modulus of the hydrated samples was determined in uniaxial tensile testing using a texturometer sold under the trade name TA-XT2 Texture Analyser by the company Stable Micro Systems, with a constant speed of 0.5 mm/s for measuring the force required until break. The curve of the strain (equal to the force in Newtons related to the surface area in $mm^2$) as a function of the strain (as %) is plotted and the Young's modulus is then calculated as being the slope at the origin in the linear part of this curve. The measurements are carried out on 3 to 5 samples for each alginate/chitosan ratio. Such a method is described for example in the article by Andersen et al., 2012, Biomacromolecules.

Stem Cell Cultures:

Cultures of rat bone marrow mesenchymal stem cells (rMSCs) were carried out in the following way:

A cell culture medium, complete alpha "Minimum Essential Medium" (MEM) (complete α MEM), was prepared by mixing 450 ml of GlutaMAX® a MEM medium sold under the reference 32561 by Gibco, 5 ml of a penicillin/streptomycin mixture (10 000 U/ml) sold under the reference 15140 by Gibco and 50 ml of foetal calf serum sold under the reference A15-043 by PAA.

The rMSCs were thawed in 15 ml of complete α MEM culture medium preheated to 37° C. After centrifugation for 5 min at 1200 rpm, the supernatant was suctioned off and then the cell pellet was taken up in 25 ml of complete α MEM culture medium. The cells were then seeded in a culture flask at a density of 10 000 cells/$cm^2$. The complete α MEM culture medium was changed every 2 to 3 days. The cells were passaged at confluence and re-seeded at a density of 10 000 cells/$cm^2$.

Evaluation of the Biocompatibility In Vitro:

The rMSCs are washed twice with 1×PBS buffer, then detached with trypsin and counted. They were then centrifuged for 5 min at 1200 rpm, and then the cell pellet was taken up in complete α MEM culture medium. 15 µl of cell suspension containing 100 000 rMSCs were deposited on the samples of polymer matrices in the dry state in a 48-well plate, centrifuged for 1 min at 400 g and at 25° C. in order to obtain uniform seeding in terms of depth and, finally, hydrated in complete α MEM culture medium. The plates were maintained under conditions of culture at 37° C. in a 5% $CO_2$ atmosphere.

Evaluation of the Cell Viability in the Polymer Matrices:

Physiological saline: solution of NaCl at 0.9% by weight in deionized water,

Fluorescent labels: viability and cytotoxicity assay kit using calcein AM and Ethidium-III, sold under the name "Viability/Cytotoxicity Assay Kit for Live & Dead Cells", reference FP-BF4710, by the company Interchim Fluo Probes®, France.

A cell-labelling solution was prepared just before use by diluting the labels to 1/10 in a 1/1 (v/v) physiological saline/α MEM culture medium mixture so as to obtain a solution of labels containing 2 µM of Ethidium-III and 1 µM of calcein AM. The labelling solution was kept in the dark until use.

The rMSCs were washed once with a 1/1 (v/v) physiological saline/α MEM culture medium mixture and then incubated with the labelling solution for 30 min at 37° C. in the dark. After incubation, the cells were washed with physiological saline and stored in physiological saline at 37° C. until observation.

The observation of the labelling was carried out using a Zeiss 780 confocal microscope: calcein AM excitation wavelength: 495 nm; calcein AM emission wavelength: 515 nm; Ethidium-III excitation wavelength: 495 nm, Ethidium-III emission wavelength: 635 nm. Successive deep images of the matrices were acquired, then a 3-dimensional reconstruction was obtained using the software associated with the microscope.

Evaluation of the Biocompatibility In Vivo:

The in vivo biocompatibility of the polymer matrices was evaluated on 3 female rats of the Lewis strain having an average weight of 200 g. For the anaesthesia, the animal was placed in a gas induction box and received a gas mixture of $O_2$+isoflurane at 4%. After total loss of the peripheral reflexes, the animal was placed on its back. The gas anaesthesia was maintained at 2% or 3% of isoflurane. A subcutaneous injection of buprenorphine (100 µg/kg) was given. The abdomen was extensively shaved, and then disinfected with 70° alcohol. After having verified the depth of the anaesthesia and the total loss of peripheral reflexes, a cutaneous incision was made in order to expose the pectoral muscles. A flexible "spreader" was inserted. The polymer matrix was slipped between 2 muscle planes. The muscle pocket was then closed with a suture using a Prolene 7/0 single thread. The spreader was removed and peritoneal cleaning was carried out. The cutaneous plane was closed again using the Ethilon 5/0 skin thread. The entire procedure was carried out by a surgeon under an operating microscope (Zeiss OPM1 FC).

Evaluation of the Angiogenic Effects In Vivo:

The in vivo angiogenic effects of the polymer matrices were evaluated on rats after intramuscular implantation of the matrices. The implantation of the matrices was carried out according to the same protocol as that used above for the evaluation of the biocompatibility in vivo. The formation of capillary vessels and of more mature vessels (arterioles) was studied after 28 days of implantation, by immunofluorescence using antibodies directed against Von Willebrand factor (VWF) making it possible to detect the endothelial cells and against smooth muscle alpha actin (α-SMA) making it possible to detect the muscles of the arterioles according to the protocols below:

Histology—Immunolabellings:

Twenty-eight days after their implantation, the matrices were removed, rinsed with physiological saline and immediately fixed with 4% paraformaldehyde (in 1×PBS, pH 7.4) for 48 h, then transferred into 70% ethanol After embedding in paraffin, histological sections 4 to 6 μm thick were cut on a microtome. Hematoxylin-eosin histological staining and anti-α-SMA (smooth muscle actin) and anti-VWF (Von Willebrand Factor) immunofluorescent labellings were carried out. For the immunofluorescence labellings, the sections on slides were first deparaffinized in xylene (3 baths of 5 min), then rehydrated in successive baths of ethanol (each 5 min) and finally in water (5 min) The antigenic sites were unmasked in a (10 mM) Tris-(1 mM) EDTA buffer containing 0.05% of Tween 20 at 121° for 3 min. The samples were then permeabilized with Triton (0.5%) and the unreacted aldehyde functions of the fixer were neutralized in a 0.1 M glycine solution (2 baths each of 10 min) The non-specific antigenic sites were saturated with a PBS buffer solution containing 2% of goat serum, 1% of bovine serum albumin and 0.2% of Triton (30 min). The slides were then labelled with an anti-α-SMA antibody (mouse anti-alpha-SMA monoclonal, A2547, Sigma, 1/1000$^{th}$ dilution) and an anti-VWF antibody (rabbit anti-human VW Factor polyclonal, A0082, Dako, 1/200$^{th}$ dilution) diluted in the saturation buffer solution. After three washes (PBS-0.2% Tween 20, each for 10 min), secondary antibodies were added: Alexa Fluor® 568 goat anti-mouse (A11019, Life Technologies) and AlexaFluor® 488 goat anti-rabbit (A11008, Life Technologies) for 30 min in the dark. After 3 washes, the nuclei were stained with DAPI (D9542, Sigma, dilution 0.05 μg/ml in PBS, 10 min) Finally, the slides were washed and mounted with a coverslip using a mounting solution for fluorescence (F4680, Sigma). All the steps were carried out is at ambient temperature.

Observation of the Immunolabellings by Confocal Microscopy

The immunolabellings were observed using a Zeiss LSM 780 confocal microscope (Carl Zeiss Microscopy) at the ×63 magnification. For each animal, the number of vessels positive for α-SMA of which the lumen is closed and of which the diameter is greater than or equal to 5 μm was counted in the area of the implant on at least 5 non-overlapping photos. Knowing the total surface area of the optical field (in mm$^2$), the density of arterioles was calculated as being equal to the number of vessels/mm$^2$ Statistics Regarding the Immunolabellings For the comparison of the number of vessels per unit of surface area between the implanted groups (L+ or reference matrices, acellular or containing MSCs), the two-sided Student's t test was used. The statistical analysis was carried out with the software sold under the trade name GraphPadPrism version 4 (PrismGraphPad, San Diego, Calif.). The Gaussian distribution of the data was tested with a normality test and the results were expressed by their mean±standard error of the mean. A test is considered to be significant if the p-value is less than 0.05.

Example 1

Preparation of Porous Polymer Matrices in Accordance with the Present Invention and of Comparative Porous Polymer Matrices which are Not Part of the Invention—Characterizations In this example, porous polymer matrices in accordance with the invention based on alginate as anionic polysaccharide and on chitosan as cationic biocompatible polymer were prepared using various alginate/chitosan weight ratios according to Table 1 below:

TABLE 1

|  | Matrix M100/0(*) | Matrix M60/40 | Matrix 50/50 | Matrix 40/60 | Matrix 0/100(*) |
|---|---|---|---|---|---|
| Alginate/chitosan weight ratio | 100/0 | 60/40 | 5050 | 40/60 | 0/100 |

(*)Comparative matrices not part of the invention

1) Preparation of the Polymer Matrices

The following compositions were prepared:

Alginate solvent (for 200 g): 1.8 g of NaCl, made up to 200 g with deionized water;

Chitosan solvent (for 100 g): 0.9 g of NaCl+1.5 g of pure acetic acid (i.e. 0.25 M) and made up to 100 g with deionized water;

Buffer I (for 1000 g): 9.0026 g of NaCl+3.2540 g of HEPES buffer, made up to 1000 g with Milli-Q® water and the pH adjusted to 7.4 with 1 M or 2 M hydrochloric acid (HCl);

Gelling buffer II (for 500 ml): 5 g of calcium chloride (i.e. 0.1 M)+50 g of pure acetic acid and made up to 500 g with Milli-Q® water (Merck) then homogenized;

Pore-forming agent tested: Sodium bicarbonate:NaHCO$_3$ (the company Sigma-Aldrich)—introduced in step 1;

Surfactant tested: Polysorbate 20 sold under the trade name Montanox® 20 DF (the company SEPPIC), introduced in step 1.

Solutions A, B, C and D, the specifications of which are given in Table 2 below, were then prepared:

TABLE 2

|  | Solutions | | | |
|---|---|---|---|---|
|  | A | B | C | D |
| Alginate solvent (g) | — | — | — | 200 |
| Alginate powder (g) | — | — | — | 6 |
| Chitosan solvent (g) | 100 | 100 | 100 | — |
| Chitosan powder (g) | 2 | 3 | 4.5 | — |

Solutions A, B, C and D were stirred at between 1600 and 1800 rpm for 60 min.

The foams having the composition indicated in Table 3 below (weight percentages) were then prepared according to the protocol previously described (steps 1 to 6 of the process in accordance with the invention):

TABLE 3

| Alginate/chitosan weight ratio | Foam 100/0(*) | Foam 60/40 | Foam 50/50 | Foam 40/60 | Foam 0/100(*) |
|---|---|---|---|---|---|
| Solution A (g) | — | 50 | — | — | — |
| Solution B (g) | — | — | 50 | — | 50 |
| Solution C (g) | — | — | — | 50 | — |
| Solution D (g) | 50 | 50 | 50 | 50 | — |

TABLE 3-continued

| Alginate/chitosan weight ratio | Foam 100/0(*) | Foam 60/40 | Foam 50/50 | Foam 40/60 | Foam 0/100(*) |
|---|---|---|---|---|---|
| Alginate solvent | 50 | — | — | — | — |
| Chitosan solvent | — | — | — | — | 50 |
| Final % alginate | 1.5 | 1.5 | 1.5 | 1.5 | 0 |
| Final % chitosan | 0 | 1 | 1.5 | 2.25 | 1.5 |
| Final % foaming agent | 0.9 | 0.9 | 0.9 | 0.9 | 0.9 |
| Final % Montanox ® 20 | 1 | 1 | 1 | 1 | 1 |

(*)Comparative matrices which are not part of the invention

The various ingredients making up the foams were mixed and the resulting compositions thus obtained were stirred at 1800 rpm for 30 minutes.

Each of the foams thus obtained was then poured into 48-well plates in a proportion of 500 µl per well, and then immediately frozen at −20° C.

After freezing, a part of the foams (called "L+") was lyophilized at a temperature of −50° C. and a pressure of between 10 and 100 µm of mercury under vacuum (according to step 3a of the process in accordance with the invention). Another part of the foams frozen (called "L−") was not subjected to this lyophilization step.

The frozen and lyophilized foams L+ and the frozen foams L− were then gelled by adding 500 µl of gelling buffer II to each of the wells, it being understood that, in order to perform the gelling of the 0/100 foam, 500 µl of a 1 M NaOH solution was used in place of the gelling buffer II, since it is known that sodium hydroxide used at this concentration causes chitosan to gel.

At the end of one hour, the plates were rinsed several times using buffer I so as to completely remove the surfactant (3 washes).

The gelled foams were then dehydrated by immersing the plates in successive baths of increasing concentration of absolute ethanol: 20%, 40% and 80% at a rate of 3 successive immersions for 10 min in each of the baths, the final dehydration having been carried out in a bath of absolute ethanol at 100% at a rate of 3 successive immersions for 15 minutes.

The gelled and dehydrated foams were then dried with supercritical $CO_2$. To do this, the foams were removed from the 48-well plates, and placed in sample racks which are placed in the chamber of an $E_{3000}$ Series Critical Point Dryer apparatus for drying with supercritical $CO_2$, from the company Quorum is Technologies. The drying with supercritical $CO_2$ was carried out at a temperature of 44° C. under a pressure of 85 bar for 25 minutes. The depressurization of the chamber was carried out at a rate of 2 bar/min until atmospheric pressure was reached. The chamber was then opened and the expected matrices were recovered.

2) Results of the Characterizations

The macroscopic appearance of the matrices thus obtained is shown in the appended FIG. 1, which represents the microscopic appearance of the internal structure of the dried or hydrated L+ matrices. The images of the dried matrices are obtained by SEM. The images of the hydrated matrices are obtained by environmental SEM by gradually increasing the level of humidity from 85% to 99%. The scale bar corresponds to 100 µm.

In this figure, FIG. 1a corresponds to the SEM photos of the dry matrices. The photos of the hydrated matrices were obtained by environmental SEM by gradually increasing the level of humidity from 85% (FIG. 1b) to 99% (FIG. 1d), FIG. 1c corresponding to an intermediate hydration state. In FIG. 1, the scale bar corresponds to 100 µm.

These photos show, in all the matrices presented, the presence of interconnected pores which open up under the effect of the rehydration; the microscopic observation makes it possible to visualize the open porosity towards the exterior of the matrices obtained.

Figure 2:
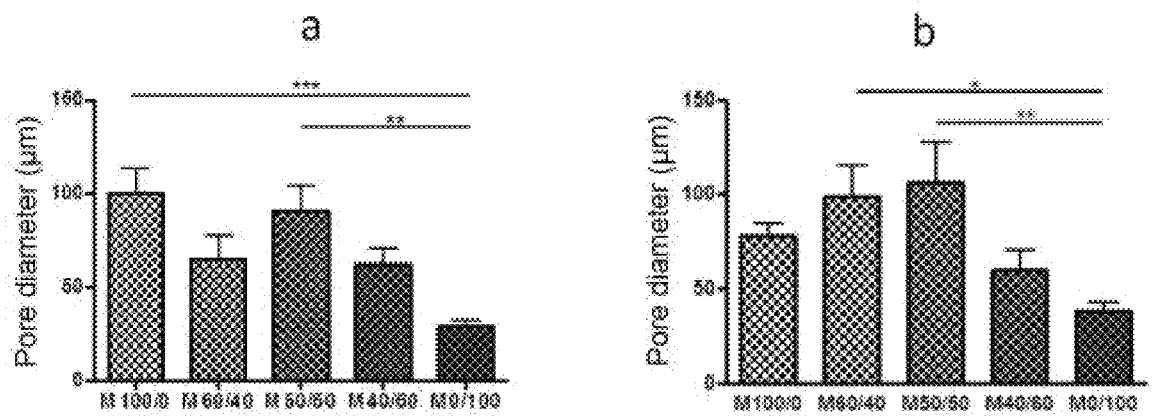
FIGS. 2a-2b are graphs of the quantitative evaluation of the porosity of the matrices obtained in example 1 in accordance with one embodiment

The quantitative evaluation of the porosity of the matrices thus obtained is given by the appended FIG. 2: quantification of the pore size of the L+ dry matrices (corresponding to the photos in FIG. 1a). The values displayed are in the form mean±standard error of the mean. The value of $p<0.05$ is considered to be significant. * $p<0.05$;  $p<0.01$; * $p<0.001$.

The surface porosity (pore diameter measured by SEM at the surface) is reported in FIG. 2a (pore diameter in µm as a function of the matrices prepared). The porosity in section (transverse diameter of the pores, measured by SEM) is reported in FIG. 2b (transverse diameter of the pores in µm as a function of matrices prepared).

The results show a similarity in porosity between alginate matrices and alginate/chitosan matrices, which overall show themselves to be superior to that of the matrices of chitosan alone, although they are all in the porosity range recognized as being favourable to cell survival and proliferation. The alginate and alginate/chitosan matrices thus appear to be more suitable for 3D-seeding.

Figure 3:
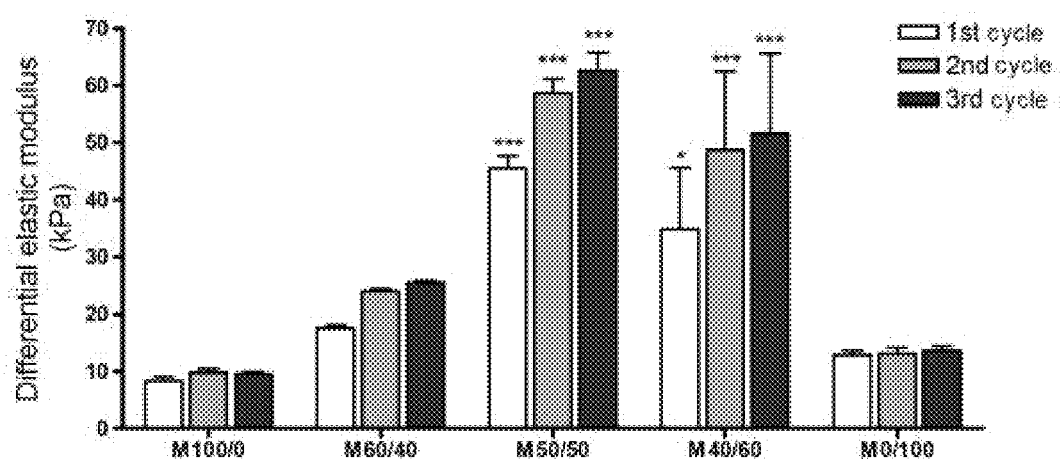
FIG. 3 is a graph of the results of compressive strength showing the mechanical compressive properties of the L+ matrices hydrated in cell culture medium from example 1 in accordance with one embodiment
Figure 4:
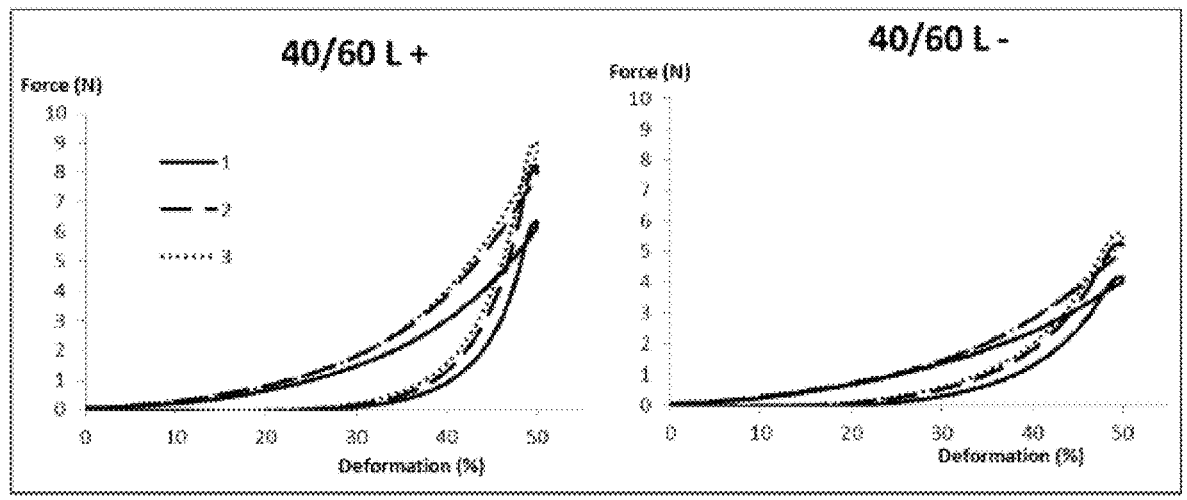
FIG. 4 is a graph comparing the results obtained with the M40/60 L+ matrix, having undergone the intermediate lyophilization step 3a, to those obtained with the M40/60 L− matrix not having undergone the step from example 1 in accordance with one embodiment FIG. 5 are photos of each of the matrices taken before and after immersion from example 2 in accordance with one embodiment

In the appended FIG. 3, the results of compressive strength are given showing the mechanical compressive properties of the L+ matrices hydrated in cell culture medium, subjected to three successive compression cycles, and also in the appended FIG. 4, which compares the results obtained with the M40/60 L+ matrix, having undergone the intermediate lyophilization step 3a, to those obtained with the M40/60 L− matrix not having undergone said step. As regards the results presented in FIG. 3, the statistical comparisons are carried out versus M100/0. * $p<0.05$; *** $p<0.001$.

In FIG. 3, the differential elastic modulus (in kPa) is as a function of the nature of the matrices prepared; the white bars correspond to the first compression cycle, the grey bars to the second compression cycle and the black bars to the third compression cycle.

In FIG. 4, the force (in Newtons, N) is as a function of the deformation (as %); the continuous-line curves correspond to the first compression cycle, the discontinuous-line curves to the second compression cycle and the dotted-line curves to the third compression cycle.

The results of FIG. 3 show the synergy associated with the interaction between the alginate and the chitosan, which results in matrices with optimized mechanical properties compared with the matrices based on alginate alone (M100/0) or on chitosan alone (M0/100). The method of drying with supercritical $CO_2$ according to step 6 of the process in accordance with the invention made it possible to obtain aerogels which retain the porosity of the foam generated in step 2) then during the gelling in step 4), and the mechanical properties associated with the formation of complexes of polyelectrolytes of opposite charges. The matrix in accordance with the invention in which the alginate/chitosan ratio is 50/50 (matrix M50/50) exhibits the best mechanical strength properties. Conversely, the matrices not in accordance with the invention (matrices M0/100 and M100/0) exhibit weaker mechanical properties which may be an impairment to their use for implantation.

The results presented in FIG. 4 show that the lyophilization step 3a, although it is optional, makes it possible to improve the mechanical properties of the matrices in accordance with the invention, the compression resistance being greater when the matrix has undergone said step.

The results of the assays for viability of the rMSCs in the matrices M0/100, M40/60 and M100/0 after 7 days of culture are reported in Table 4 below:

TABLE 4

| Alginate/chitosan ratio | L⁻ matrices | L⁺ matrices |
|---|---|---|
| M100/0(*) | + | + |
| M40/60 | ++ | ++ |
| M0/100(*) | ++ | + |

(*)Comparative matrices which are not part of the invention

In Table 4, the "+" signs relate to the presence of live cells (cells which appear green when observed with a confocal microscope because they are stained with calcein AM). The number of "+" relates to the number of detectable live cells. All the matrices contain live cells after 7 days of culture, which demonstrates the biocompatibility of the matrices in accordance with the invention.

Finally, it emerges from the tests for evaluating the biocompatibility after implantation in rats (evaluation 1 week after intra-muscular implantation at the pectoral level) that:

the matrices obtained by means of the process in accordance with the invention lend themselves well to surgical manipulation and to implantation without this damaging them;

the implantation of the matrices does not cause the animals to experience any impairment in terms of moving, feeding, etc.;

the implantation does not cause any massive inflammatory reaction or any other physiological reaction that might endanger the health of the animals having undergone implantation;

one week after their implantation, the matrices are kept in place (at the site of implantation) and retain their integrity (no matrix debris).

Example 2

Study of the Behaviour with Respect to Rehydration of Two Matrices in Accordance with the Present Invention In this example, the behaviour with respect to rehydration of the M40/60 matrix in accordance with the invention which had undergone an intermediate lyophilization step 3a, as prepared according to the process described above in Example 1 (M40/60 L⁺ matrix), was compared with that of the M40/60 matrix in accordance with the invention but which had not undergone this intermediate lyophilization step 3a, as also prepared according to the process described above in Example 1 (M40/60 L⁻ matrix).

Figure 5:
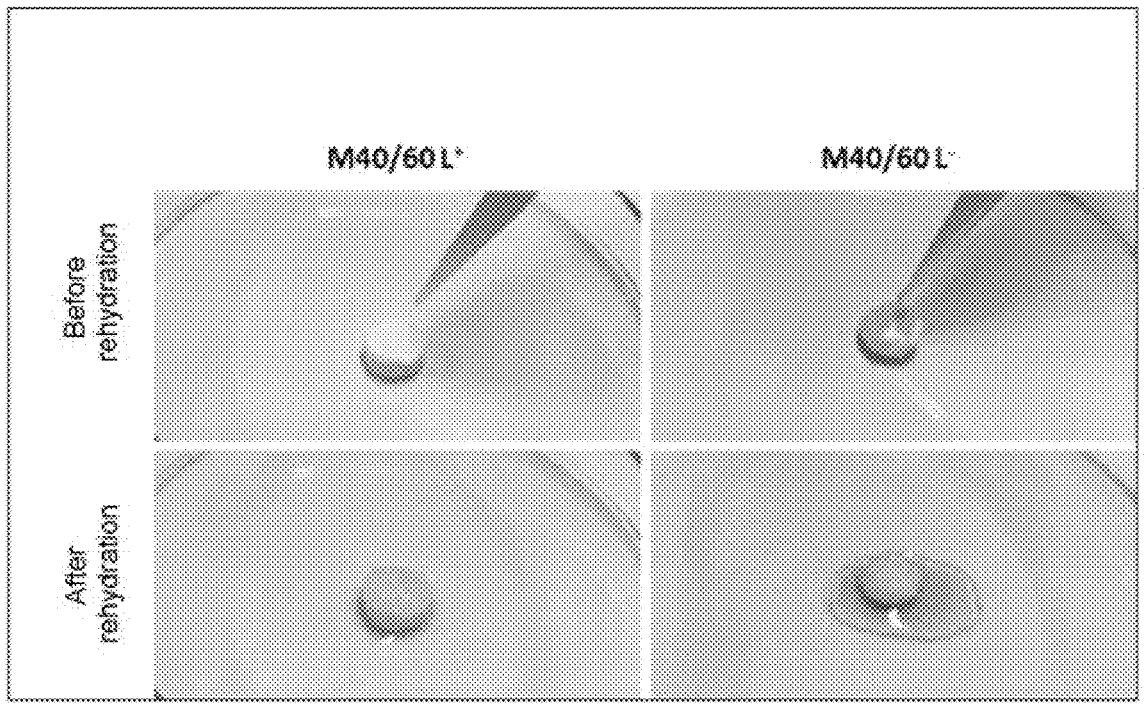

To do this, samples of identical diameter of each of these two matrices were immersed in water for 5 min. Photos of each of the matrices taken before and after immersion are given in the appended FIG. 5.

It can be observed that the M40/60 L⁺ matrix having undergone the intermediate lyophilization step 3a of the process in accordance with the invention swells faster in water and reaches its definitive swelling level (maximum hydration state) in less than 5 min, whereas the M40/60 L⁻ matrix not having undergone said step swells more slowly and does not reach its maximum hydration level within this period. Consequently, these results show that, although it is optional, this intermediate lyophilization step makes it possible to improve the rehydration properties of the matrices in accordance with the invention.

Example 3

Evaluation of the Angiogenic Effects of a Matrix in Accordance with the Invention Compared with a Matrix Not in Accordance with the Present Invention In this example, the angiogenic effects of the M40/60 L⁺ matrix in accordance with the invention and as prepared above in Example 1 were evaluated in comparison with those of a matrix not in accordance with the invention, obtained according to a preparation process identical in all respects to that of the M40/60L⁺ matrix, except that the last two steps of dehydration and drying with supercritical $CO_2$ were replaced with a further freezing step and then a further lyophilization step, said steps being carried out under the same conditions as the steps for freezing the foam and for lyophilizing the frozen foam, described above in Example 1. Said matrix, which is therefore doubly lyophilized, is called M40/60 REF.

Each of these two matrices was tested after implantation without multiplication in rats (M40/60 L⁺ matrix in accordance with the invention and M40/60 REF matrix not in accordance with the invention), and also after prior seeding with 500 000 rMSCs (M40/60 L⁺-MSC matrix in accordance with the invention and M40/60 REF-MSC matrix not in accordance with the invention). Each matrix was tested on 2 rats.

The evaluations were carried out after 28 days of implantation.

Figure 6:
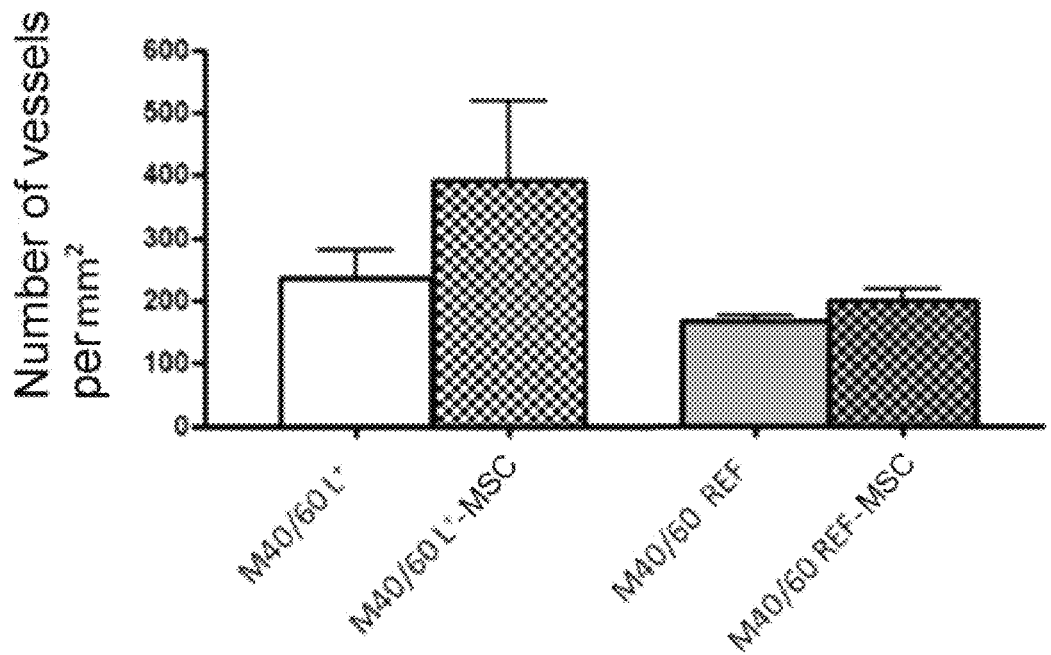
FIG. 6 is a graph that gives the number of α-SMA-positive vessels per $mm^2$ after 28 days of implantation for each of the matrices tested from example 3 in accordance with one embodiment.

The appended FIG. 6 gives the number of α-SMA-positive vessels per $mm^2$ after 28 days of implantation for each of the matrices tested.

Fluorescence microscope observations (not represented) showed that the M40/60 L⁺ matrix implanted is richly vascularized and that the vessels are distributed throughout the whole granular tissue which forms following biodegradation thereof. The vessels present in the matrices are functional (because they contain red blood cells). In the presence of these rMSCs seeded in the matrix, the vascularization of the latter is greater (237±44 vessels per $mm^2$ in the M40/60 L⁺ group compared with 391±127 vessels per $mm^2$ in the 40/60 L⁺-MSC group). In the case of the M40/60 REF matrix not in accordance with the invention, the same trend is observed in the presence of MSCs (166±11 vessels per $mm^2$ compared with 199±21 vessels per $mm^2$) However, it is noted that the vascularization of the M40/60 REF matrix is significantly less abundant than that of the M40/60 L⁺ matrix dried with supercritical $CO_2$ in accordance with the present invention.

These tests demonstrate that the choice of the final step of drying with supercritical $CO_2$ is not a simple alternative to a lyophilization step, but, on the contrary, this drying method influences the properties of the resulting matrix, in particular its angiogenic properties after implantation.

The invention claimed is:

1. Process for preparing a biocompatible and biodegradable polymer matrix comprising a network of open and interconnected pores, said process comprising at least the following steps:
   1) preparing an aqueous solution comprising at least one biocompatible anionic polysaccharide chosen from alginates and modified alginates; and at least one biocompatible cationic polymer chosen from chitosan, chitosan salts and chitosan derivatives, 2) mechanically stirring said solution obtained above in the preceding step, in the presence of a foaming agent or of a pressurized gas, so as to form a foam, 3) freezing the foam obtained above in the preceding step, so as to obtain a frozen foam, 4) gelling the frozen foam obtained above in the preceding step, by adding, to said foam, at least one gelling agent in solution in a solvent, so as to obtain a gelled foam, 5) dehydrating the gelled foam obtained above in the preceding step, so as to obtain a dehydrated gelled foam, then 6) drying the dehydrated gelled foam obtained above in the preceding step, by treatment with supercritical $CO_2$, so as to obtain said polymer matrix.

2. Process according to claim 1, wherein the biocompatible anionic polysaccharide(s) have an average molecular weight (MwA) of greater than or equal to 75 000 Daltons.

3. Process according to claim 1, wherein the amount of anionic polysaccharides present in the aqueous solution of step 1) ranges from 0.5% to 8% by weight relative to the total weight of said aqueous solution.

4. Process according to claim 1, wherein the biocompatible cationic polymer(s) have an average molecular weight ($Mw_C$) of greater than or equal to 100 000 Daltons.

5. Process according to claim 1, wherein the amount of cationic polymers present in the aqueous solution of step 1) ranges from 0.5% to 15% by weight relative to the total weight of said aqueous solution.

6. Process according to claim 1, wherein the weight ratio of anionic polysaccharides ($W_{AP}$)/cationic polymers ($W_{CP}$) present in the aqueous solution of step 1) ranges from 20/80 to 80/20.

7. Process according to claim 1, wherein the aqueous solution prepared during step 1) also comprises at least one hydrophilic surfactant.

8. Process according to claim 7, wherein the hydrophilic surfactant(s) represent from 0.01% to 5% by weight relative to the total weight of the aqueous solution of step 1).

9. Process according to claim 1, wherein the foam is formed in the presence of a foaming agent which is therefore added to the solution prepared in step 1) just before carrying out step 2).

10. Process according to claim 1, wherein, during step 2), the foam is formed by introducing a pressurized gas into the aqueous solution prepared in step 1).

11. Process according to claim 1, wherein the freezing step 3) is followed by a step 3a) of lyophilizing the foam obtained at the end of step 3).

12. Process according to claim 1, wherein the gelling agent used during step 4) of gelling the frozen foam is a solution of at least one salt of a divalent or trivalent cation in a solvent.

13. Process according to claim 1, wherein step 6) of drying, with supercritical $CO_2$, the dehydrated foam obtained at the end of step 5) is carried out at a temperature ranging from 35 to 50° C., and at a pressure ranging from 45 to 95 bar.

* * * * *